United States Patent [19]

Bengtsson et al.

[11] 4,229,595
[45] Oct. 21, 1980

[54] METHOD OF PRODUCING NITRO-PHENOLS

[75] Inventors: Erik Bengtsson; Boris Holm, both of Karlskoga, Sweden

[73] Assignee: Aktiebolaget Bofors, Bofors, Sweden

[21] Appl. No.: 945,367

[22] Filed: Sep. 25, 1978

[30] Foreign Application Priority Data

Oct. 7, 1977 [SE] Sweden ............................ 7712088

[51] Int. Cl.² .............................................. C07C 79/26
[52] U.S. Cl. .................................................... 568/706
[58] Field of Search .................... 568/706, 708, 710

[56] References Cited

U.S. PATENT DOCUMENTS

| | | | |
|---|---|---|---|
| 3,510,527 | 5/1970 | Prosser | 568/706 |
| 3,642,913 | 2/1972 | Callister et al. | 568/706 |
| 3,917,719 | 11/1975 | Baldwin et al. | 568/706 |
| 3,933,926 | 1/1976 | Salter | 568/707 |

Primary Examiner—Werren B. Lone
Attorney, Agent, or Firm—Pollock, Vande Sande & Priddy

[57] ABSTRACT

Preparation of nitro compounds of phenols and alkyl substituted derivatives thereof which includes nitrosating phenols or alkyl derivative thereof, oxidizing the nitroso compound, separating off nitrogen oxides, separating nitro compounds from reaction mixture, and subjecting mother liquor and washing liquids to destructive oxidation at elevated temperatures and recycling nitrogen oxides and nitric acid.

22 Claims, 1 Drawing Figure

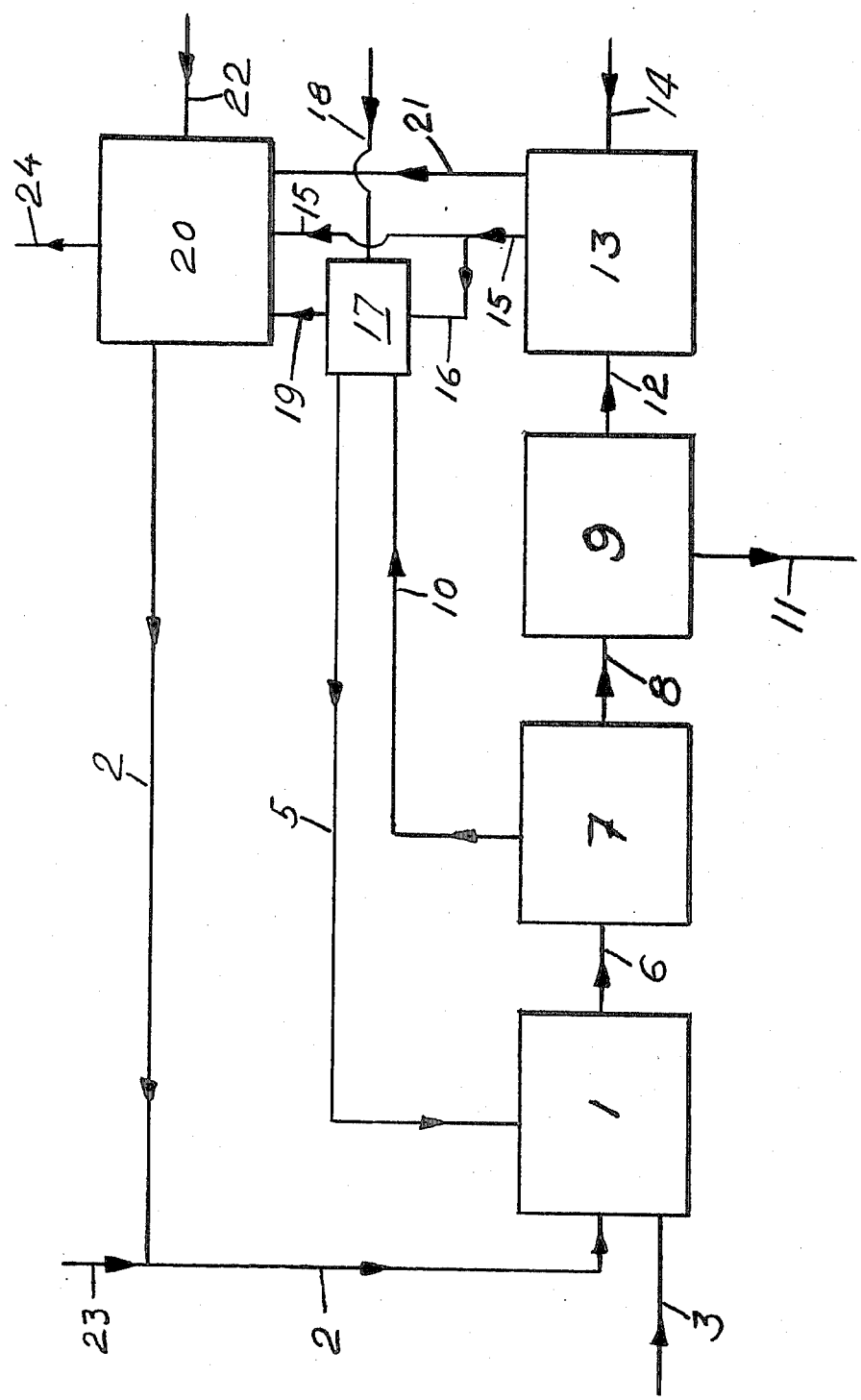

METHOD OF PRODUCING NITRO-PHENOLS

The present invention relates to a method of producing nitro-phenols and then particularly in a way which is satisfactory from an environmental point of view, starting from unsubstituted or alkyl-substituted phenols. As an example of a technically important nitro-phenol may be mentioned p-nitro-m-cresol, which is an important raw material for certain insecticides.

As direct nitration of phenols gives a poor yield and large quantities of by-products, nitro-phenols have been manufactured for a long time by the phenol first having been nitrosated, after which the nitroso compound is oxidized. Even with this method, difficulties are encountered in the form of poor yields and a considerable formation of by-products. It has therefore, inter alia, been proposed to carry out the oxidation after the nitrosation in the presence of methyl and ethyl alcohol, but without being able to arrive at any satisfactory method.

For the above-mentioned important raw material of p-nitro-m-cresol, special methods have also been developed over e.g. the intermediate product tricresyl phosphate, which is nitrated, and thereafter hydrolyzed. This last-mentioned method is not acceptable either, as among other things, it is very complicated and costly to carry out, and like the previously mentioned methods, it has considerable disadvantages from an environmental point of view.

Waste water, mother liquors and waste products containing phenols and nitro-phenols are very troublesome from an environmental point of view, and a prerequisite for a production with present-day requirements for exterior and interior environment is that no emission of such products takes place. Further, the process must be carried out in such a way that the operating personnel is protected from contact with these substances.

Through the present invention, the above-mentiond disadvantages have been eliminated, and a method which is entirely satisfactory from an environmental point of view has been created.

The characteristic feature of the invention is that at the production of nitro compounds, starting from unsubstituted or alkyl-substituted phenols, in a way which is known in itself, these are nitrosated in a nitric acid solution through treatment with nitrogen oxides, after which the nitroso-compound after an increase of the temperature of the nitric acid is oxidized to the nitro compound, at which oxidation nitrogen oxides are separated off, and which nitro compound through cooling and filtering is thereafter separated from the reaction mixture, and that the mother liquor and washing liquids, if any, are subjected to destructive oxidation with nitric acid at an elevated temperature and an increased pressure so that the mother liquor and washing liquids, if any, after emitting nitrogen oxides, carbon dioxide and possible nitrogen, will substantially contain only nitric acid and water, and that the nitric acid and nitrogen oxides from both the oxidation stage and the destruction stage, after a possible addition of air, are returned to the reaction system and are used for new nitrosation and destruction, whereby from the reaction system, besides the nitro compound formed, substantially only water, carbon dioxide and possibly nitrogen will be emitted.

The nitrosation is carried out with the use of $NO_2(N_2O_4)$, $N_2O_3$ and/or $NO$ to which has been added an adapted quantity of air, and at a temperature of between $+10°$ and $-30°$ C., preferably at somewhat below $0°$ C. At the beginning of the nitrosation, the concentration of nitric acid should amount to between 10 and 35 percent by weight, preferably to approx. 20 percent by weight, and the nitrosation should be carried on between 15 minutes and 1 hour, preferably during approx. 30 minutes.

The oxidation should appropriately be carried out at a temperature of between $20°$ and $45°$ C., preferably at approx. $30°$ C., and should be allowed to continue for between 30 minutes and 3 hours, preferably for approx. 2 hours.

The destructive oxidation should be carried out at a temperature exceeding $130°$ C. and at a pressure exceeding 15 kg/cm$^2$, preferably at approx. $190°$-$200°$ C. and 30-45 kg/cm$^2$, and using a nitric acid with a concentration of between 15 and 65 percent by weight, preferably approx. 30-40 percent by weight, and should be carried on for at least 10 minutes, preferably for approx. 40 minutes.

The reaction can be carried out in batches or continuously, in batch reactors directly connected with each other, where the nitrosation, oxidation, separation of the nitro compound and the destructive oxidation are carried out in different reactors. Alternatively, both the nitrosation and the oxidation and possibly also the destructive oxidation can be carried out in tube reactors, and the nitrosation and oxidation can then be carried out in one and the same tube reactor, the nitrosation then being carried out in the front part of the reactor and the oxidation in the latter part.

The method can appropriately be used for the production of p-nitro-m-cresol.

The schematic construction of a device for carrying out the method according to the present invention will be noted from the accompanying block diagram.

To the reactor 1 in which the nitrosation is to be carried out, nitric acid can be conveyed via the pipe 2, phenol via the pipe 3 and nitrogen oxides via the pipe 5. From the reactor 1, after the nitrosation has been completed, the reaction mixture can be transferred via the pipe 6 to the reactor 7 and after completed oxidation through the pipe 8 to the reactor 9. During the oxidation, nitrogen oxides are conveyed off through the pipe 10. In the reactor 9 the nitro compound formed is separated, and is conveyed off through the pipe 11, while the remaining mother liquid is conveyed via the pipe 12 to the reactor 13, where the destructive oxidation is carried out. In order that the concentration of nitric acid desired may be obtained at the destructive oxidation, nitric acid may be added via the pipe 14.

During the destructive oxidation in the reactor 13, nitrogen oxides, carbon dioxide and possible nitrogen are conveyed off through the pipe 15. Some nitrogen oxides, particularly $N_2O_4$, are separated—possibly through a cooling procedure—and are conveyed off through the pipe 16. The nitrogen oxides conveyed off through the pipe 16 and the nitrogen oxides which through the pipe 10 come from the oxidation reactor 7 are transferred to the nitrogen oxide treatment plant 17, and after air has possibly been added via the pipe 18, and thereafter conveyed through the pipe 5 to the nitrosation reactor 1. The nitrogen oxides which cannot appropriately be used for the nitrosation go via the pipes 15 and 19 to the nitric acid recovery plant 20. To this nitric acid recovery plant 20 is also conveyed through the pipe 21, after separation of gases, liquid containing nitric acid from the reactor 13, where the destructive oxidation has been carried out. Through the pipe 22, air and water can be added to the nitric acid recovery plant 20, so that from this, through the pipe 2, nitric acid appropriate for the nitrosation can be conveyed to the reactor 1. Complementary nitric acid can possibly be added via the pipe 23. In the plant 20, all nitrogen oxides are absorbed, and only carbon dioxide and possibly nitrogen are emitted through the pipe 24.

As will be noted from the block diagram, besides the nitrophenol formed there is emitted (via the pipe 11) in principle only carbon dioxide and possibly nitrogen (via the pipe 24). To the system is conveyed, besides phenol (via the pipe 3) only nitric acid (via the pipes 14 and 23) and air and water (via the pipe 22). In this way, a method which is satisfactory from an environmental point of view has been created.

The invention will be further illustrated through the following examples.

EXAMPLE 1

A reaction apparatus with a stirrer was charged with 84 ml of 99% nitric acid and 540 ml water, and the mixture was cooled to 0° C. Thereafter, at one and the same time, 54 g of m-cresol and 53 g of liquid $N_2O_3$ were added. The temperature was kept through cooling the whole time below 5° C. After the addition of m-cresol and $N_2O_3$ had been completed, the stirring was continued for 1 hour, the temperature then being kept at approx. 0° C. Thereafter the temperature was allowed to rise to approx. 30° C., and at that temperature the stirring was continued for 2 hours. The reaction mixture was thereafter cooled to 0° C. and a solid product was then precipitated. This solid product was then filtered off, washed with water and dried. In this way, 70 g of raw p-nitro-m-cresol with a melting point of 118°–122° C. was obtained.

The raw product can thereafter in a conventional way be freed from o-isomers through distillation in water vapour, possibly complemented with re-precipitation by being dissolved in a sodium hydroxide solution, followed by acidification with hydrochloric acid or nitric acid. Purification can also take place by means of recrystallization from e.g. toluene or through distillation in vacuum.

300 ml of a mother liquor obtained after separating off nitro-cresol as described above was charged into a digestor. Thereafter 127 g of 99% nitric acid was added, so that the content of nitric acid in the mixture became 35%. The temperature was thereafter raised to 220° C., and the pressure then rose to approx. 45 kg/cm². The reaction was thereafter allowed to continue at this temperature and this pressure for 40 minutes. After the destructive oxidation carried out in this way, the content of organic material in the reaction mixture amounted to less than 0.1%.

EXAMPLE 2

The reaction was carried out in the same way as described in example 1, but with the difference that the charge consisted of 42 ml of 99% nitric acid and 540 ml of water, which was cooled to −3° C., after which 46 g of liquid $N_2O_3$ was added. This was followed by cooling to −10° C., and 54 g of m-cresol was added, and during the whole of the time the temperature was kept below −5° C., by cooling. After stirring for 30 minutes at −5° C., the reaction mixture was heated to 35° C., and was kept at this temperature, with stirring, for 1.5 hours.

After cooling to approx. 15° C., a solid product was precipitated, which was filtered off, washed with water and dried. The product consisted of 59 g of raw p-nitro-m-cresol, and had a melting point of 120.5°–123.5° C.

EXAMPLE 3

Also this reaction was carried out, in principle, in the same way as example 1, but with the following differences:

21 ml of 99% nitric acid and 580 ml of water was cooled to −5° C. Thereafter 46 g of liquid $NO_2(N_2O_4)$ was added slowly. The mixture was thereafter cooled to −10° C., after which 54 g of m-cresol was added while the reaction temperature, through cooling, was kept below −5° C. After stirring for 30 minutes at −10° C., the reaction mixture was heated to 35° C., and was kept at this temperature, with stirring, for a further 2 hours. The crystalline product precipitated after cooling to 0° C., after filtering off, washing with water and drying consisted of 61 g of raw p-nitro-m-cresol with a melting point of 118°–122° C.

EXAMPLE 4

This example differs from the procedure according to example 1 in the following respects:

21 ml of 99% nitric acid and 580 ml of water was cooled to −2° C., after which 46 g of liquid $NO_2(N_2O_4)$ was added. While keeping the temperature, through cooling, at −5° C., 47 g of phenol dissolved in 50 ml of water was thereafter added. The reaction mixture was stirred for 1 hour at −5° C., and the temperature was thereafter raised to 20° C. and the stirring continued at this temperature for 30 minutes. After cooling to 5° C. a solid product was precipitated, which was filtered off and washed with water. After drying, 49 g of raw p-nitro-phenl was obtained.

Successful trials have also been carried out at which the nitrosation has been carried out with the acid of NO which has been obtained at previous oxidation and to which an appropriate quantity of air has been added. The method has also proved to be useful for chlorine-substituted phenols, and tests with directly connected batch reactors or tube reactors have given results corresponding to the tests described above.

Finally, it has proved to be possible to vary the method in different ways within the scope of the patent claims. Thus, for instance, the nitroso compound has been isolated before the oxidation, nitrosation and/or oxidation has been carried out under pressure, and the mother liquor obtained has to a certain extent been returned to the system and circulated.

We claim:

1. A method of producing mono-nitro compounds of monohydric phenol and alkyl substituted derivatives of monohydric phenol which comprises nitrosating said phenol or alkyl substituted derivative of phenol in a nitric acid solution through treatment with nitrogen oxides at temperatures of between +10° and −30° C.;
   oxidizing the nitroso compound at a temperature of between 20° and 45° C. after an increase of the temperature of the nitric acid;
   separating off nitrogen oxides during said oxidizing;
   separating the nitro compound from the reaction mixture through cooling and filtering;
   subjecting the mother liquor and washing liquids to destructive oxidation with nitric acid at a temperature exceeding 130° C. and an increased pressure so that the mother liquor and washing liquids after emitting at least nitrogen oxides and carbon dioxide will substantially contain only nitric acid and water;

and returning the nitric acid and nitrogen oxides from both the oxidation stage and the destruction stage and using them for new nitrosation and destruction, whereby from the reaction system, is formed said nitro compounds and in addition, substantially only water, carbon dioxide and possibly nitrogen will be emitted.

2. A method according to claim 1 characterized in that the nitrosation is carried out with the use of $NO_2(N_2O_4)$ or $N_2O_3$ or NO or mixtures thereof.

3. A method according to claim 1 or claim 2 characterized in that the nitrosation is carried out at a temperature below 0° C.

4. A method according to claim 1 or claim 2 characterized in that the concentration of nitric acid at the beginning of the nitrosation amounts to between 10 and 35 percent by weight.

5. A method according to claim 1 or claim 2 characterized in that the nitrosation is carried on for between 15 minutes and 1 hour.

6. A method according to claim 1 or claim 2 characterized in that the oxidation is carried out at approx. 30° C.

7. A method according to claim 1 or claim 2 characterized in that the oxidation is carried on for between 30 minutes and 3 hours.

8. A method according to claim 1 or claim 2 characterized in that the destructive oxidation is carried out at a pressure exceeding 15 kg/cm$^2$.

9. A method according to claim 1 or claim 2 characterized in that for the destructive oxidation a nitric acid is used with a concentration of between 15 and 65 percent by weight.

10. A method according to claim 1 or claim 2 characterized in that the destructive oxidation is carried on for at least 10 minutes.

11. A method according to claim 1 or claim 2 characterized in that the reaction is carried out in batches.

12. A method according to claim 1 or claim 2 characterized in that the reaction is carried out continuously in batch reactors directly connected with each other, in which the nitrosation, oxidation, separation of the nitro compound and the destructive oxidation are carried out in different reactors.

13. A method according to claim 1 or claim 2 characterized in that both the nitrosation and the oxidation are carried out in tube reactors.

14. A method according to claim 13, characterized in that the nitrosation and oxidation are carried out in one and the same tube reactor, the nitrosation then being carried out in the front part of the reactor and the oxidation in the latter part.

15. A method according to claim 1 or claim 2 characterized in that it is used for the production of p-nitro-m-cresol.

16. The method of claim 1 wherein nitrogen is also emitted.

17. The method of claim 4 wherein said concentration of nitric acid amounts to approximately 15 percent by weight.

18. The method of claim 5 wherein said nitrosation is carried out for approximately 30 minutes.

19. The method of claim 7 wherein said oxidation is carried on for approximately 2 hours.

20. The method of claim 8 wherein the destructive oxidation is carried out at a temperature of approximately 190°–200° C. and a pressure of 30–45 kg/cm$^2$.

21. The method of claim 9 wherein said nitric acid has a concentration of approximately 30–40 percent by weight.

22. The method of claim 10 wherein said destructive oxidation is carried on for approximately 40 minutes.

* * * * *

UNITED STATES PATENT AND TRADEMARK OFFICE
CERTIFICATE OF CORRECTION

PATENT NO. : 4,229,595
DATED : October 21, 1980
INVENTOR(S) : Erik Bengtsson and Boris Holm It is certified that error appears in the above-identified patent and that said Letters Patent are hereby corrected as shown below:

Foreign Application Priority Data

October 27, 1977 [SE]   Sweden ................7712088

Signed and Sealed this

Seventeenth Day of February 1981

[SEAL]

Attest:

RENE D. TEGTMEYER

Attesting Officer    Acting Commissioner of Patents and Trademarks